(12) United States Patent
Blazecka et al.

(10) Patent No.: US 7,935,817 B2
(45) Date of Patent: May 3, 2011

(54) SALT FORM AND COCRYSTALS OF ADEFOVIR DIPIVOXIL AND PROCESSES FOR PREPARATION THEREOF

(75) Inventors: Peter Garth Blazecka, Brantford (CA); Daqing Che, Taizhou (CN); Cameron L. McPhail, Brantford (CA); Allan W. Rey, Brantford (CA)

(73) Assignee: Apotex Pharmachem Inc., Brantford (CA)

( * ) Notice: Subject to any disclaimer, the term of this patent is extended or adjusted under 35 U.S.C. 154(b) by 490 days.

(21) Appl. No.: 12/059,321

(22) Filed: Mar. 31, 2008

(65) Prior Publication Data

US 2009/0247749 A1 Oct. 1, 2009

(51) Int. Cl.
*C07F 9/6561* (2006.01)
*A61K 31/675* (2006.01)

(52) U.S. Cl. ...................................... 544/244
(58) Field of Classification Search .................. 540/244; 514/81
See application file for complete search history.

(56) References Cited

U.S. PATENT DOCUMENTS

| | | | | |
|---|---|---|---|---|
| 4,362,730 A * | 12/1982 | Rader et al. | ............ | 514/283 |
| 4,521,412 A * | 6/1985 | Schmitt et al. | ............ | 514/244 |
| 4,614,649 A * | 9/1986 | Gorman et al. | ............ | 424/54 |
| 4,724,233 A | 2/1988 | De Clercq | | |
| 4,808,716 A | 2/1989 | Hol | | |
| 4,894,239 A * | 1/1990 | Nonomura et al. | ............ | 424/497 |
| 6,451,340 B1 | 9/2002 | Arimilli | | |
| 6,635,278 B1 | 10/2003 | Dahl | | |
| 6,723,343 B2 * | 4/2004 | Kugelmann | ............ | 424/479 |
| 7,053,192 B2 * | 5/2006 | Li et al. | ............ | 536/7.4 |
| 2004/0224917 A1 * | 11/2004 | Dahl et al. | ............ | 514/47 |
| 2005/0135999 A1 * | 6/2005 | Elomari et al. | ............ | 423/706 |
| 2006/0020011 A1 * | 1/2006 | Wu et al. | ............ | 514/406 |
| 2006/0025384 A1 | 2/2006 | Wang | | |
| 2006/0243831 A1 * | 11/2006 | Gonzalez-Zugasti et al. | .. | 241/23 |
| 2007/0032435 A1 * | 2/2007 | Alani et al. | ............ | 514/18 |
| 2007/0249544 A1 * | 10/2007 | Himmelsbach et al. | ............ | 514/27 |
| 2008/0004448 A1 * | 1/2008 | Wayne et al. | ............ | 546/276.7 |
| 2008/0089835 A1 * | 4/2008 | Burton | ............ | 423/706 |
| 2008/0103186 A1 * | 5/2008 | Glover et al. | ............ | 514/395 |
| 2008/0139569 A1 * | 6/2008 | Rocco et al. | ............ | 514/248 |
| 2008/0161324 A1 * | 7/2008 | Johansen et al. | ............ | 514/255.03 |
| 2008/0319024 A1 * | 12/2008 | Greil et al. | ............ | 514/342 |
| 2009/0069281 A1 * | 3/2009 | Austad et al. | ............ | 514/183 |
| 2009/0124652 A1 * | 5/2009 | Ach et al. | ............ | 514/293 |
| 2009/0137794 A1 * | 5/2009 | Mendez et al. | ............ | 540/78 |
| 2009/0176983 A1 * | 7/2009 | Dova et al. | ............ | 544/242 |
| 2009/0203705 A1 * | 8/2009 | Biagetti et al. | ............ | 514/252.02 |
| 2009/0239946 A1 * | 9/2009 | McKeown et al. | ............ | 514/494 |
| 2010/0021539 A1 * | 1/2010 | Kowalski et al. | ............ | 424/464 |
| 2010/0087488 A1 * | 4/2010 | Pop et al. | ............ | 514/338 |

FOREIGN PATENT DOCUMENTS

| | | | |
|---|---|---|---|
| CA | 2514733 | | 9/2004 |
| CN | 1425680 A | * | 6/2003 |
| CN | 1528766 A | * | 9/2004 |
| CN | 1569861 A | * | 1/2005 |
| CN | 1603331 A | * | 4/2005 |
| CN | 1879635 | | 12/2006 |
| CN | 101544670 A | * | 9/2009 |
| WO | WO 9904822 A2 | * | 2/1999 |
| WO | WO00/12067 | | 3/2000 |
| WO | WO 2000012067 A1 | * | 3/2000 |
| WO | WO 2005094832 A1 | * | 10/2005 |

OTHER PUBLICATIONS

Liu, Rong, ed., Water-Insoluble Drug Formulation (CRC Press, 2008) Chapter 15 pp. 417-435.*
Bastin et al., Organic Process Research & Development 2000, 4, 427-435.*
Morris, et al., International Journal of Pharmaceutics 105 (1994) 209-217.*
Adeyeye, Moji, ed., Preformulation in Solid Dosage Form Development (Informa Healthcare, 2008) Chapter 2.3, pp. 63-80.*
Gould, International J. of Therapeutics 33, 201 (1986).*
Serajuddin, Advanced Drug Delivery Reviews 59 (2007) 603-616.*
Swarbrick et al., eds. Encyclopedia of Pharmaceutical Technology 13 (Marcel Dekker, NY 1996) pp. 453-499.*
Banerjee, Crystal Growth & Design, 2005, 5 (6), pp. 2299-2309.*
Gray, Appl Microbiol. Jul. 1953; 1(4): 211-213.*
Yuan, L-C et al., Pharmaceutical Research, (2000) vol. 17, No. 9, p. 1098-1103.
Thayer, AM, "Form and Function. The choice of pharmaceutical . . . ", Chemical & Engineering News, (Jun. 18, 2007), vol. 85, No. 25, pp. 17-30.

* cited by examiner

*Primary Examiner* — Mark L Berch

(57) ABSTRACT

Provided are a cocrystal of Adefovir dipivoxil and nicotinamide as well as a cocrystal of Adefovir dipivoxil and salicylamide cocrystal and processes for the preparation thereof.

22 Claims, 8 Drawing Sheets

SALT FORM AND COCRYSTALS OF ADEFOVIR DIPIVOXIL AND PROCESSES FOR PREPARATION THEREOF

FIELD OF THE INVENTION

The invention relates to a novel salt form and cocrystals of adefovir dipivoxil and processes for the preparation thereof.

BACKGROUND

Adefovir dipivoxil, with trade names Preveon® and Hepsera®, is a diester prodrug of adefovir. Adefovir is an orally-administered nucleotide analog reverse transcriptase inhibitor (ntRTI) used for treatment of hepatitis B.

The chemical name of adefovir dipivoxil is 9-[2-[[bis[(pivaloyloxy)methoxy]phosphinyl]-methoxy]ethyl]adenine. It has a molecular formula of $C_{20}H_{32}N_5O_8P$, a molecular weight of 501.48 g/mol and the following structural formula:

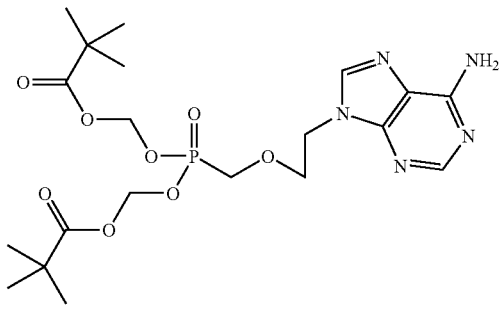

Processes for the manufacture of adefovir and adefovir dipivoxil have been described in U.S. Pat. Nos. 4,724,233, 4,808,716 and 6,451,340.

Adefovir dipivoxil is unstable to moisture and can degrade to several degradation products (Yuan et al., Pharmaceutical Research, Vol. 17, 1098-1103, 2000; U.S. Pat. No. 6,635,278). Therefore, desiccants such as silica gel or activated charcoal are typically required as packaging aids (U.S. Pat. No. 6,635,278). Adefovir dipivoxil has an aqueous solubility of 19 mg/mL at pH 2.0 and 0.4 mg/mL at pH 7.2. It has an octanol/aqueous phosphate buffer (pH 7) partition coefficient (log p) of 1.91.

The crystalline form of an active pharmaceutical ingredient profoundly affects its physical properties such as solubility, stability, dissolution rate and bioavailability.

Pharmaceutical cocrystals are attractive because they offer multiple opportunities to modify the chemical and/or physical properties of an active pharmaceutical ingredient (API) without making or breaking covalent bonds.

Novel pharmaceutical salt forms of adefovir dipivoxil having expected and improved properties are beneficial. The pharmaceutical properties of an API can be significantly altered by salt formation. For example, salt formation can lead to changes in organoleptic properties (taste acceptability) as well as solubility, stability (hydrolytic, photolytic, thermal, hygroscopic), permeability, compactability, and processability of the parent molecule. These changes can lead to improved bioavailability, manufacturability, stability and patient compliance. A saccharinate salt form, for example, may offer special advantages such as improved taste acceptability. Salt formation and the resulting alteration in performance of the salt compared to the parent compound is not predictable.

CA 2,514,733 contains a very lengthy list of compounds (including Adefovir) and possible co-crystal forming agents. However, details are only provided for selected examples such as Celecoxib:nicotinamide, Olazapine:nicotinamide, Itraconazole:succinic acid, Itraconazole:fumaric acid, Itraconazole:L-tartrate, Itraconazole:malic acid, Itraconazole hydrochloride:DL tartaric acid, Modafinil:malonic acid, Modafinil:glycolic acid, Modafinil:maleic acid, Fluorouracil:urea, Carbamazepine:nicotinamide, Carbamazepine:saccharin. Similar to other solid forms such as solvated or hydrated forms, cocrystal formation is not predictable.

For the foregoing reasons, there is a need for novel crystalline forms of adefovir dipivoxil with enhanced chemical and physical properties.

SUMMARY

The present invention is directed to novel crystalline forms of adefovir dipivoxil.

In one embodiment the novel crystalline forms are novel cocrystals and salt forms of adefovir dipivoxil with enhanced stability as compared to adefovir dipivoxil alone.

In another embodiment, the novel crystalline form is a novel salt of adefovir dipivoxil with enhanced stability as compared to adefovir dipivoxil alone.

In another embodiment adefovir dipivoxil forms a nicotinamide cocrystal, preferably in a 1:1 mole ratio of adefovir dipivoxil:nicotimamide.

Another embodiment is that adefovir dipivoxil forms a salicylamide cocrystal, preferably in a 1:1 mole ratio of adefovir dipivoxil:salicylamide.

Another embodiment is that adefovir dipivoxil forms a saccharin salt, preferably in a 1:1 ratio of adefovir dipivoxil:saccharin.

We have found that adefovir dipivoxil:nicotinamide cocrystals possess enhanced physical properties when compared to other forms of adefovir dipivoxil. For example, we have discovered that ADE:NIC cocrystals exhibit improved thermal stability compared to amorphous adefovir dipivoxil. For example, following storage at 40° C./75% relative humidity, the HPLC purity of amorphous adefovir dipivoxil decreased by 1% per week over 2 weeks, whereas ADE:NIC showed no decrease after 1 week and decreased by only 0.06% after a prolonged 4 week storage period under the same conditions. We have also found that adefovir dipivoxil:salicylamide (hereafter "ADE:SLA") cocrystals possess enhanced chemical and physical properties as compared to adefovir dipivoxil alone.

In another aspect, there is provided a process for the preparation of adefovir dipivoxil:nicotinamide cocrystal (ADE:NIC) (a) comprising forming a solution of adefovir dipivoxil and nicotinamide in a suitable solvent at an appropriate temperature; (b) promoting crystal growth and (c) collecting the crystals, preferably by filtration and drying, preferably drying at elevated temperature.

Preferably, the solvent is selected from the group consisting of $C_3$-$C_{12}$ alkanoic acid esters such as ethyl acetate and isopropyl acetate; $C_3$-$C_7$ alkyl ketones such as acetone and methyl isobutyl ketone; cyclic and acyclic aliphatic ethers such as methyl tert-butyl ether; and $C_1$-$C_8$ alkanols such as isopropanol; and mixtures thereof. More preferably, the solvent is selected from the group consisting of ethyl acetate, isopropyl acetate, methyl tert-butyl ether, acetone, methyl isobutyl ketone, isopropanol and mixtures thereof. Preferably the amount of nicotinamide is from 1 to 5 mole equivalent with respect to adefovir dipivoxil. Preferably, dissolution of adefovir dipivoxil and nicotinamide is performed at elevated temperatures. More preferably, the temperature is from about 20° C. to about 70° C. The ADE:NIC cocrystals are then allowed to form, preferably by cooling, more preferably by cooling to a temperature of about 20° C. to about 40° C. The ADE:NIC cocrystals are then collected, preferably by filtration and drying. Preferably, the drying is performed in vacuo, preferably at elevated temperatures, more preferably at 30-50° C.

In another embodiment, the ADE:NIC cocrystal exhibits a PXRD spectrum as shown in FIG. 1. Preferably the ADE:NIC cocrystal exhibits a powder X-ray diffraction ("PXRD") spectrum using Cu—K.alpha radiation expressed in degrees 2 theta showing peaks at about 3.6, 7.2, 8.6, 9.1, 10.0, 10.9, 13.7, 15.2, 16.9, 18.2, 20.1, 21.2, 23.7, 24.9, 26.2, 27.7 and 29.3.

In another embodiment the ADE:NIC cocrystal exhibits a Fourier Transform Infrared (FTIR) spectrum as shown in FIG. 2. Preferably the ADE:NIC cocrystal exhibits a FTIR absorption spectrum (1% KBr) exhibiting peaks expressed in $cm^{-1}$ at about 3421, 3194, 1753, 1647, 1602, 1475, 1400, 1267, 1141 and 962.

In another embodiment the ADE:NIC cocrystal exhibits a Differential Scanning Calorimetry (DSC) thermogram as shown in FIG. 3. Preferably the ADE:NIC cocrystal exhibits a DSC thermogram having a peak endotherm at a peak onset temperature of about 100° C. and a peak maximum of about 103° C.

In another aspect of the present invention, there is provided a process for the preparation of adefovir dipivoxil:salicylamide (ADE:SLA) cocrystal comprising (a) forming a solution of adefovir dipivoxil and salicylamide in a suitable solvent at an appropriate temperature; (b) promoting crystal growth and (c) collecting the crystals, preferably by filtration and drying, preferably drying at elevated temperature.

Preferably, the solvent is selected from the group consisting of $C_3$-$C_{12}$ alkanoic acid esters such as ethyl acetate; $C_3$-$C_7$ alkyl ketones such as acetone; and cyclic and acyclic aliphatic ethers such as methyl tert-butyl ether; and mixtures thereof. More preferably, the solvent is selected from the group consisting of ethyl acetate, acetone, methyl tert-butyl ether and mixtures thereof. Preferably, the amount of salicylamide is from 1 to 5 mole equivalents with respect to adefovir dipivoxil. Preferably, dissolution of adefovir dipivoxil and salicylamide is performed at elevated temperatures. More preferably, the temperature is from about 20° C. to about 65° C. The ADE:SLA cocrystals are then allowed to form, preferably by cooling, more preferably by cooling to a temperature of about 20° C. to about 40° C. The ADE:SLA cocrystals are then collected, preferably by filtration and drying. Preferably, the drying is performed in vacuo, preferably at elevated temperatures, more preferably at 30-50° C.

In another embodiment the ADE:SLA cocrystal exhibit a PXRD spectrum as shown in FIG. 4. Preferably the ADE:SLA cocrystal exhibits a PXRD spectrum using Cu—K.alpha radiation expressed in degrees 2 theta showing peaks at about 3.3, 6.5, 9.8, 11.9, 12.5, 13.1, 15.0, 15.5, 16.4, 17.7, 21.9, 22.8, 23.6, 24.0, 26.0, 26.8 and 28.3.

In another embodiment the ADE:SLA cocrystal exhibits a FTIR spectrum as shown in FIG. 5. Preferably the ADE:SLA cocrystal exhibits a FTIR absorption spectrum (1% KBr) exhibiting peaks expressed in $cm^{-1}$ at about 3411, 3162, 2987, 1755, 1677, 1603, 1415, 1271, 1154 and 972.

In another embodiment the ADE:SLA cocrystal exhibits a DSC thermogram as shown in FIG. 6. Preferably the ADE:SLA cocrystal exhibits a DSC thermogram having a peak endotherm at a peak onset temperature of about 108° C. and a peak maximum of about 109° C.

We have also found that adefovir dipivoxil forms a novel salt with saccharin; namely adefovir dipivoxil saccharinate (ADE:SAC) preferably having a 1:1 stoichiometry. This new salt form possesses enhanced physical properties as compared to other forms of adefovir dipivoxil. For example, we have discovered that ADE:SAC salt exhibits improved thermal stability compared to amorphous adefovir dipivoxil. Following storage at 40° C./75% relative humidity, the HPLC purity of amorphous adefovir dipivoxil decreased by 1% per week over 2 weeks, whereas ADE:SAC showed no decrease after 1 week and decreased by only 0.06% after a prolonged 4 week storage period under the same conditions.

In another aspect, a process is provided for preparation of adefovir dipivoxil saccharin salt comprising (a) forming a solution of adefovir dipivoxil and saccharin in a suitable solvent at an appropriate temperature; (b) promoting crystal growth; and (c) collecting the salt, preferably in crystal form by filtration and drying, preferably drying at elevated temperature.

According to another embodiment of the invention, the solvent is selected from the group consisting of $C_3$-$C_{12}$ alkanoic acid esters such as ethyl acetate; $C_3$-$C_7$ alkyl ketones such as acetone; and $C_1$-$C_8$ alkanols such as isopropanol; and mixtures thereof. Preferably, the solvent is selected from the group consisting of ethyl acetate, acetone, ethanol and mixtures thereof. Preferably the amount of saccharin is from 1 to 5 mole equivalent with respect to adefovir dipivoxil. Preferably, dissolution of adefovir dipivoxil and saccharin is performed at elevated temperatures. More preferably, the temperature is from about 20° C. to about 50° C. The ADE:SAC salt is then allowed to form, preferably by cooling, preferably to a temperature of about 20° C. to about 40° C. The cocrystals are then collected, preferably by filtration and drying. Preferably, the drying is performed in vacuo, preferably at elevated temperatures, more preferably at 30-50° C.

In another embodiment, the adefovir dipivoxil and saccharin salt exhibits a PXRD spectrum as shown in FIG. 7. Preferably the adefovir dipivoxil and saccharin salt exhibits a PXRD spectrum using Cu—K.alpha radiation expressed in degrees 2 theta showing peaks at about 3.5, 7.1, 10.6, 14.2, 16.4, 17.0, 18.3, 18.7, 20.3, 21.6, 23.1, 24.1, 25.0, 26.8, 27.9, 29.7 and 30.3.

In another embodiment is adefovir dipivoxil and saccharin salt exhibits a FTIR spectrum as shown in FIG. 8. Preferably the adefovir dipivoxil and saccharin salt exhibits a FTIR absorption spectrum (1% KBr) exhibiting peaks expressed in $cm^{-1}$ at about 3209, 3127, 2979, 1752, 1698, 1632, 1584, 1287, 1148 and 957.

These and other features, aspects, and advantages of the present invention will become better understood with regard to the following description, appended claims and accompanying drawings.

BRIEF DESCRIPTION OF THE DRAWINGS

The following figures illustrate preferred and alternative embodiments of the invention, wherein.

DESCRIPTION

Adefovir dipivoxil forms novel cocrystals and a salt with other compounds. Adefovir dipivoxil and nicotinamide form a cocrystal (ADE;NIC) in a 1:1 ratio. Adefovir dipivoxil and salicylamide form a cocrystal (ADE:SLA) in a 1:1 ratio. Adefovir dipivoxil and saccharin form a salt (ADE:SAC) in a 1:1 ratio.

The adefovir dipivoxil:nicotinamide cocrystal and the adefovir dipivoxil:salicylamide cocrystal and adefovir dipivoxil:saccharin salt are characterized by means of $^1$H NMR, IR, DSC and PXRD.

Preparation of ADE:NIC Cocrystals

EXAMPLES

The X-ray powder diffraction patterns of the individual cocrystals were recorded with a PANalyticaX'Pert Pro MPD diffractometer with fixed divergence slits and an X'Celerator™ RTMS detector. The diffractometer was configured in Bragg-Brentano geometry; data was collected over a 2 theta range of 3-40 using CuKa radiation at a power of 40 mA and 45 kV. CuK.beta. radiation was removed using a divergent beam nickel filter. A step size of 0.017 degrees and a step time of 20 seconds were used. Samples were rotated to reduce preferred orientation effects.

Example 1

Figure 2:
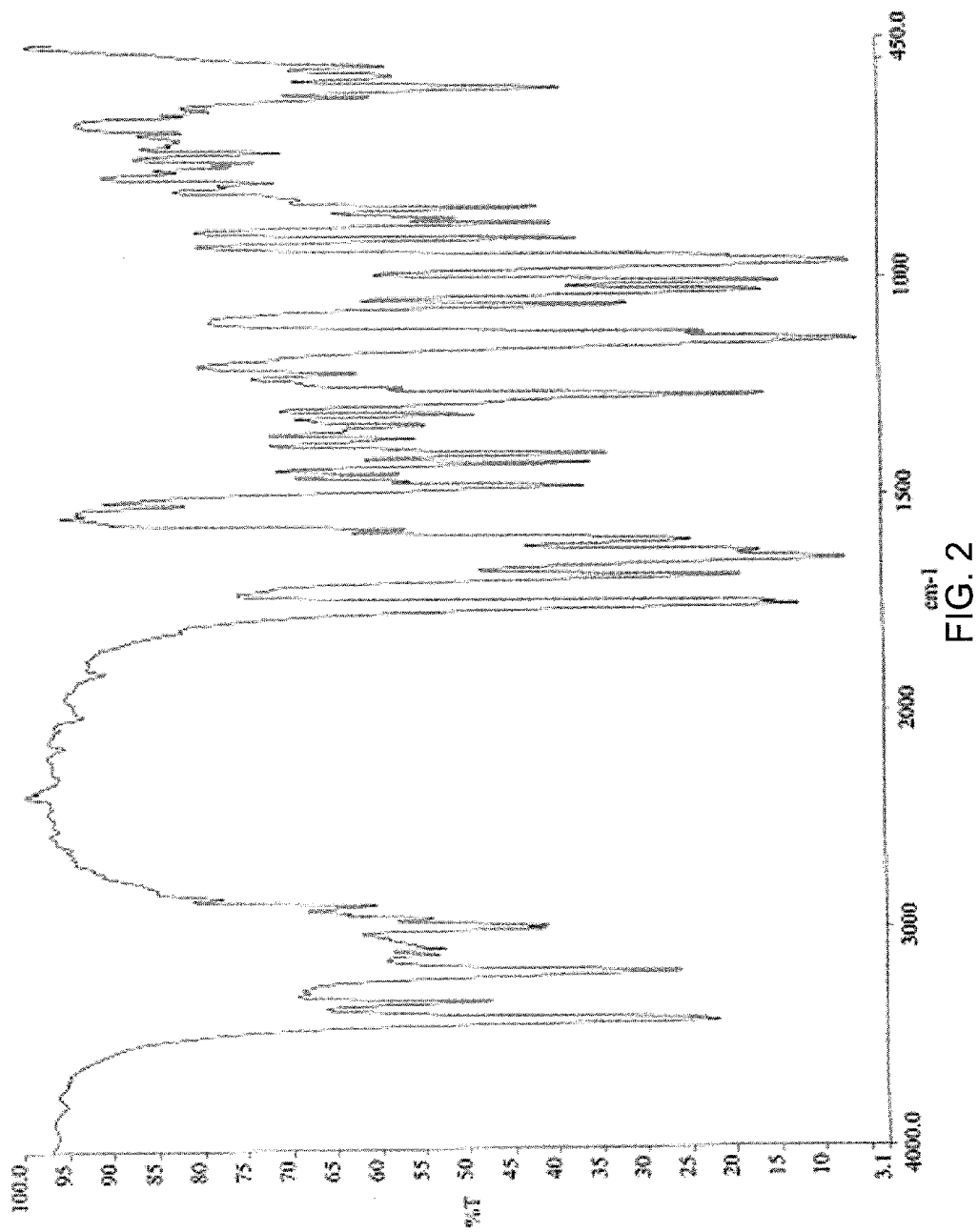
FIG. 2 shows a Fourier transform infrared absorption spectrum of ADE:NIC cocrystals.

Adefovir dipivoxil (3.00 g, 0.0060 moles) and nicotinamide (0.74 g, 1.01 equivalents) were combined with 10 mL IPA and the mixture was warmed to a point above room temperature to effect dissolution, about 50-60° C. The stirred solution was allowed to cool to room temperature. Stirring at room temperature was continued for sufficient time to allow cocrystallization to occur, about 50 minutes. The mixture was diluted with 30 mL MTBE and stirred an additional 17 hours. The cocrystals were collected by suction filtration and dried in vacuo (35-40° C.) to yield 2.73 g (70%) of ADE:NIC cocrystals. $^1$H NMR spectrum (CDCl$_3$, 300 MHz) δ 9.06 (m, 1H), 8.76 (m, 1 H), 8.34 (s, 1H), 8.20 (m, 1H), 7.94 (s, 1H), 7.41 (m, 1H), 6.54 (br s, 2H), 6.00 (br s, 2H), 5.62-5.70 (m, 4H), 4.40 (t, 2H), 3.95 (t, 2H), 3.86 (d, 2H) and 1.21 (s, 18H). FTIR as shown in FIG. 2.

Example 2

Figure 1:
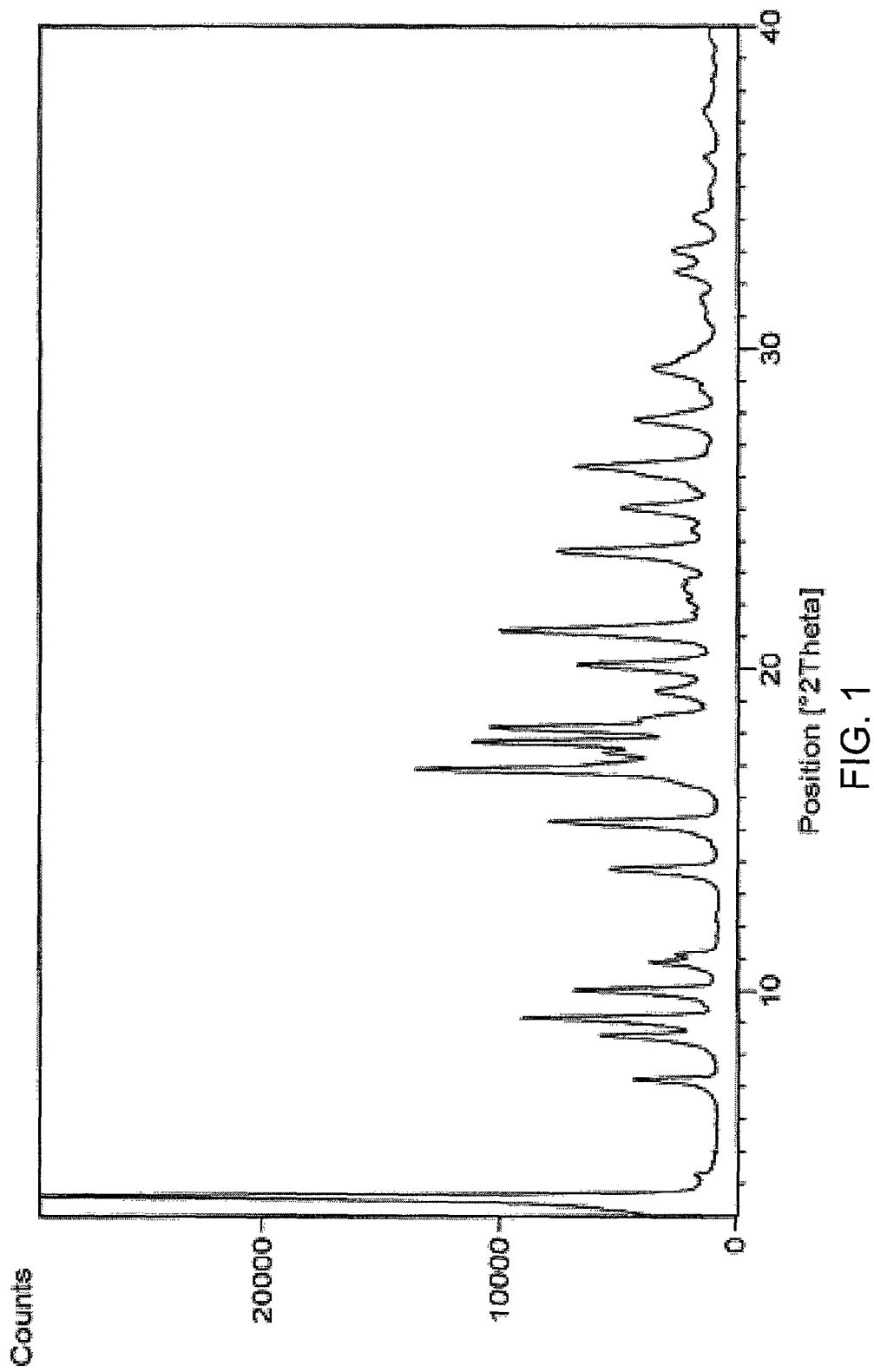
FIG. 1 shows a powder X-ray diffraction pattern of ADE:NIC cocrystals.

A 100 mL round bottom flask was charged with 5.01 g adefovir dipivoxil (0.0100 moles), followed by 1.23 g nicotinamide (1.01 equivalents) and 50 mL ethyl acetate. The mixture was stirred and heated to 65-70° C. A clear solution was achieved after 15 minutes at which time the heating was stopped. The solution was allowed to passively cool to room temperature. During the cooling phase, about 1 hour, the precipitation of a white solid was observed. The resulting slurry was stirred at room temperature for 24 hours. The crystalline solid was collected by suction filtration and dried in vacuo (40-45° C.) affording 5.00 g (80%) of ADE:NIC cocrystals. PXRD as shown in FIG. 1.

Example 3

Figure 3:
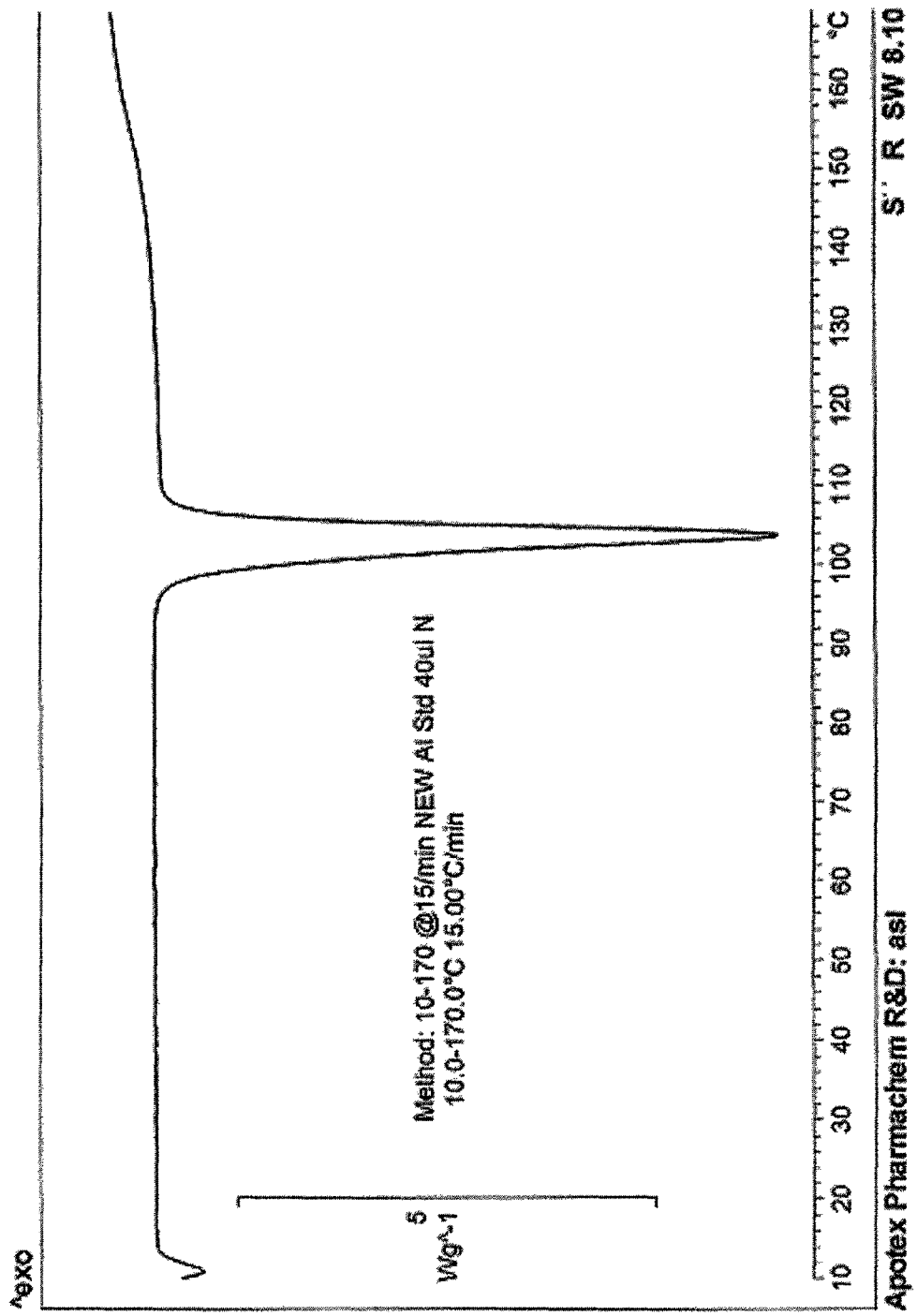
FIG. 3 shows a differential scanning calorimetry thermogram of ADE:NIC cocrystals.

A 2 L round bottom flask was charged with 90.00 g adefovir dipivoxil (0.1795 moles), 22.14 g nicotinamide (1.01 equivalents) and 900 mL ethyl acetate. The mixture was heated to 50-55° C. with moderate agitation over a period of 45 minutes. Complete dissolution was achieved during this time whereupon heating was terminated and the solution was cooled to room temperature over 4 hours. Precipitation of a white solid occurred during the cool-down period. Agitation at room temperature was continued for 16 hours. The solid was isolated by suction filtration and dried in vacuo (35-40° C.) to give 88.23 g (79%) of ADE:NIC cocrystals. DSC as shown in FIG. 3.

Preparation of ADE:SLA Cocrystals

Example 4

Figure 5:
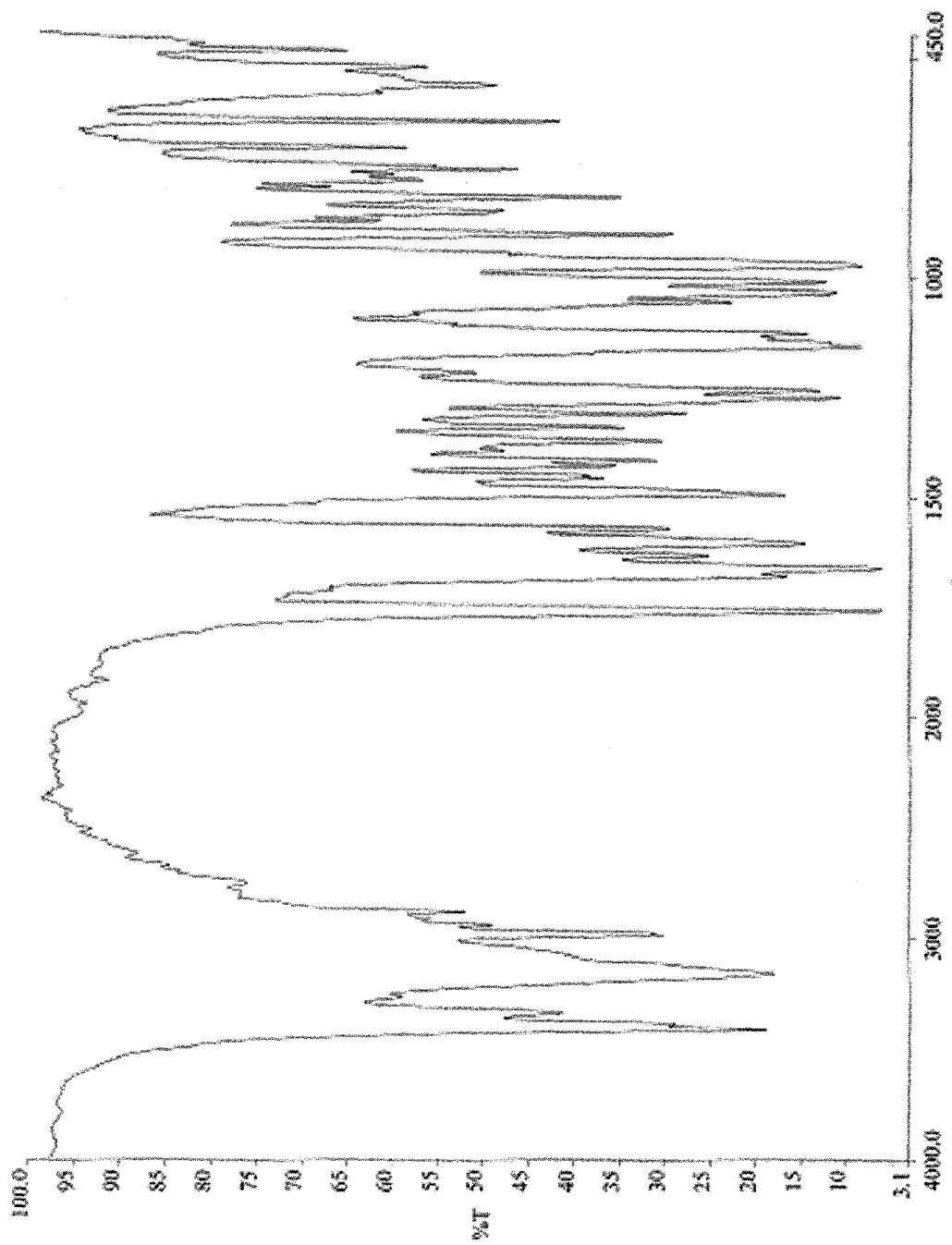
FIG. 5 shows a Fourier transform infrared absorption spectrum of ADE:SLA cocrystals.

A mixture of 1.00 g adefovir dipivoxil (0.0020 moles), 1.37 g salicylamide (5.0 equivalents), 50 mL MTBE and 5 mL acetone in a 100 mL single-neck round bottom flask was heated to reflux with moderate agitation. All solid dissolved after about 10 minutes. The heating was stopped and the solution was allowed to cool to room temperature. Stirring at room temperature was continued for 40 hours during which time a white solid precipitated. The solid was collected by suction filtration and dried in vacuo (20-25° C.) affording 1.00 g (78%) of ADE:SLA cocrystals. $^1$H NMR (CDCl$_3$, 300 MHz) δ 12.26 (br s, 1H), 8.34 (s, 1H), 7.93 (s, 1H), 7.40-7.45 (m, 2H), 7.00 (m, 1H), 6.86 (m, 1H), 6.44 (br s, 2H), 5.93 (br s, 2H), 5.62-5.70 (m, 4H), 4.40 (t, 2H), 3.94 (t, 2H), 3.86 (d, 2H) and 1.21 (s, 18H). FTIR as shown in FIG. 5.

Example 5

Figure 4:
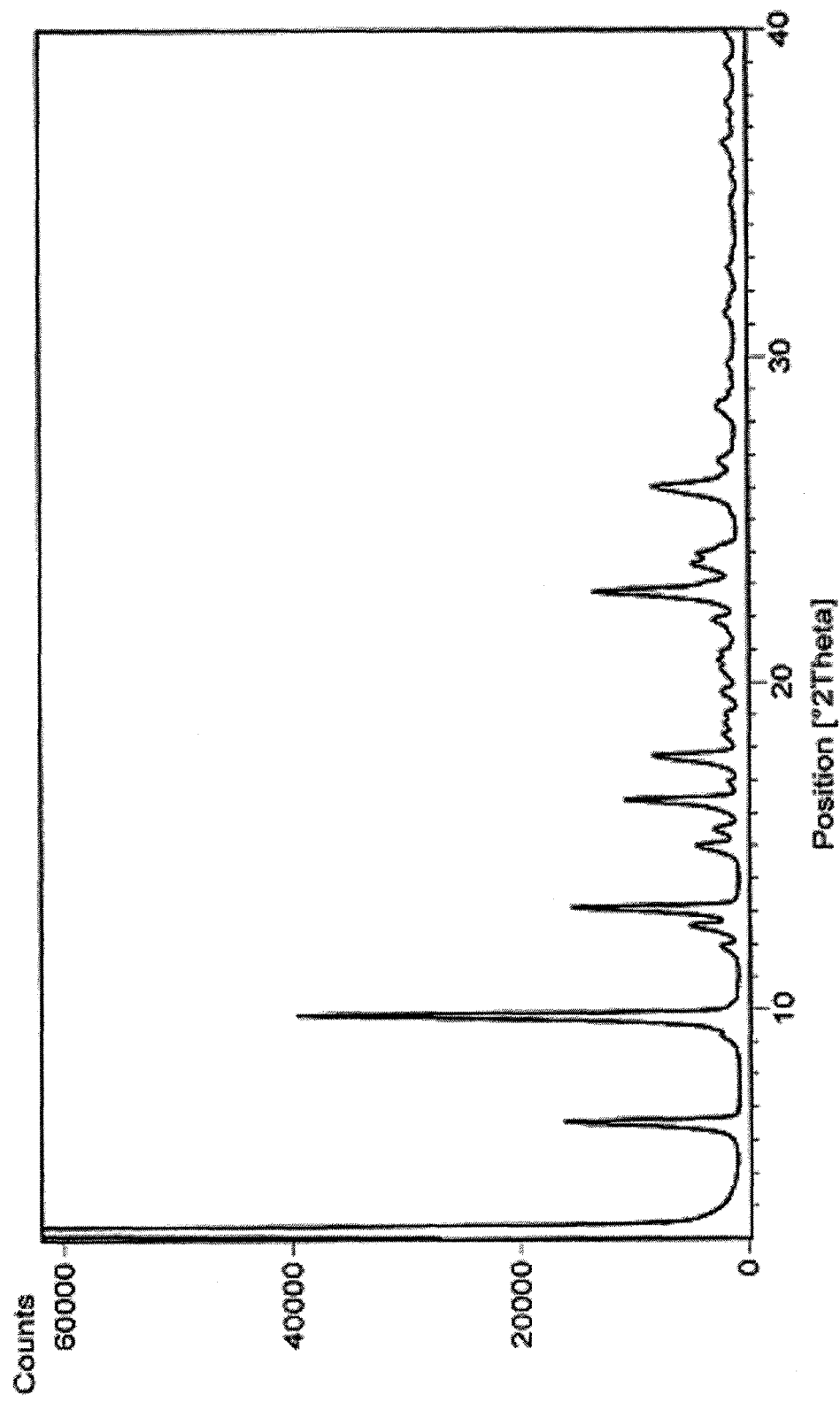
FIG. 4 shows a powder X-ray diffraction pattern of ADE:SLA cocrystals.
Figure 6:
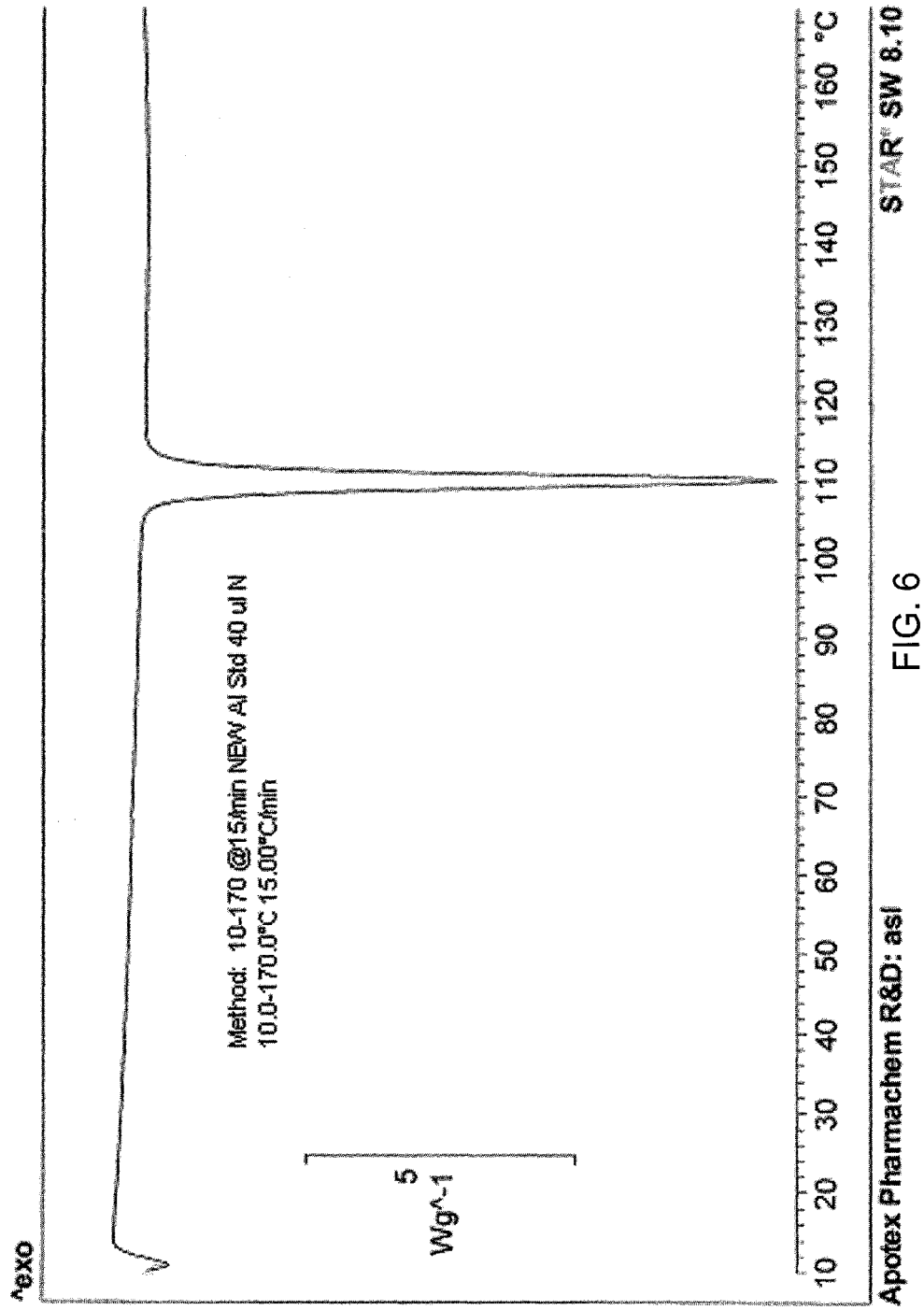
FIG. 6 shows a differential scanning calorimetry thermogram of ADE:SLA cocrystals.

A 100 mL round bottom flask containing a mixture of 5.01 g adefovir dipivoxil (0.0100 moles), 1.39 g salicylamide (1.01 equivalents) and 30 mL ethyl acetate was heated to 60-65° C. over about 5 minutes. The slurry became a solution at this elevated temperature. The stirred solution was cooled to room temperature over 1 hour. Upon additional agitation for 2 hours a white precipitate formed. The mixture was diluted with 20 mL MTBE and the solid was collected by suction filtration and dried in vacuo (35-40° C.) yielding 5.00 g (78%) of ADE:SLA cocrystals. PXRD as shown in FIG. 4. DSC as shown in FIG. 6.

Preparation of ADE:SAC Salt

Example 6

Adefovir dipivoxil (1.00 g, 0.0020 moles) and saccharin (0.37 g, 1.01 equivalents) were combined with 10 mL acetone and the mixture was stirred at room temperature during which time dissolution occurred. Stirring at room temperature was continued for sufficient time to allow salt formation to occur. The salt crystals were collected by suction filtration and dried in vacuo affording 0.71 g (52%) of ADE:SAC salt. $^1$H NMR (CDCl$_3$, 300 MHz) δ 8.39 (s, 1H), 8.27 (s, 1H), 7.85-7.91 (m, 2H), 7.68-7.76 (m, 2H), 5.63-5.72 (m, 4H), 4.48 (t, 2H), 4.02 (t, 2H), 3.91 (d, 2H) and 1.21 (s, 18H).

Example 7

Figure 7:
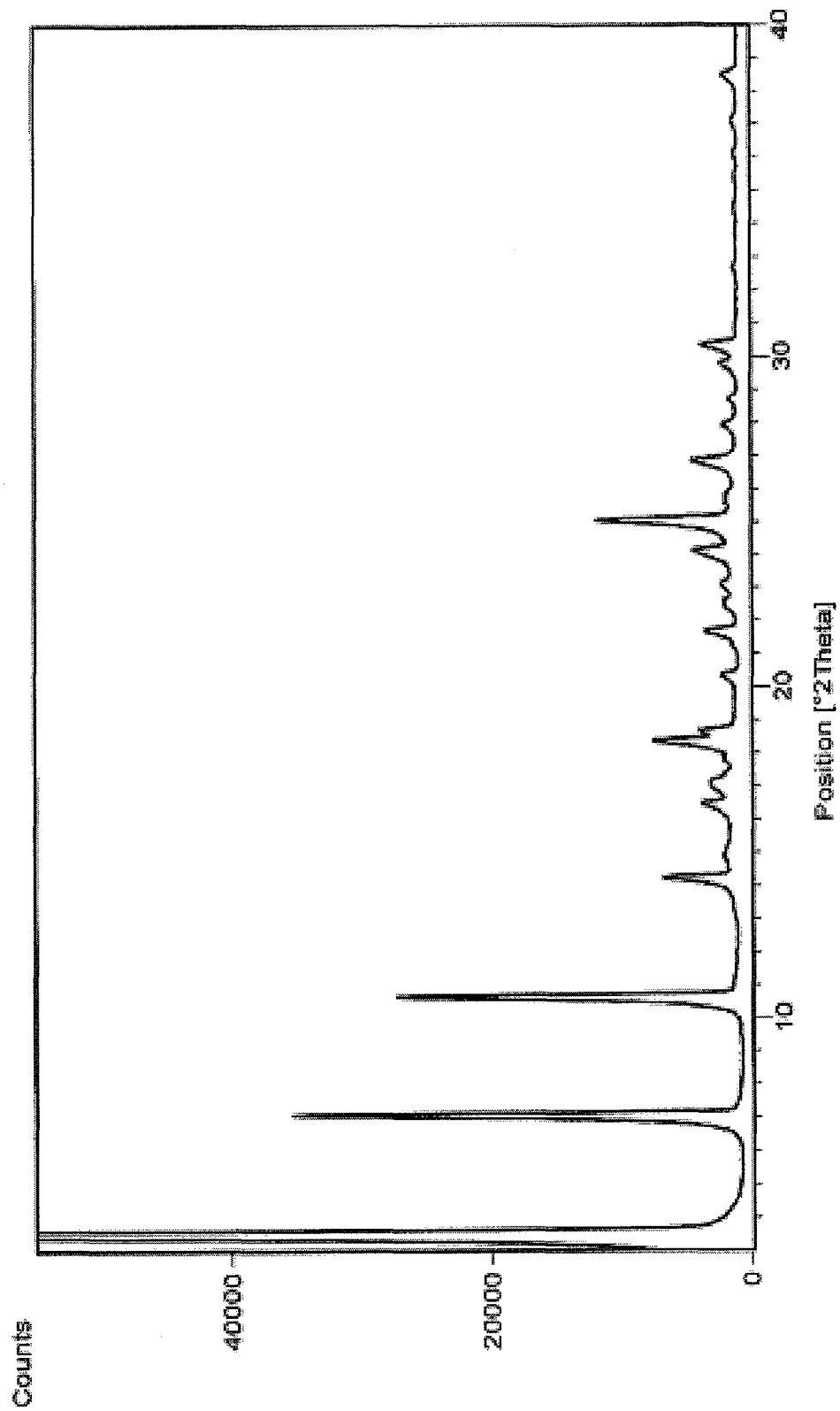
FIG. 7 shows a powder X-ray diffraction pattern of ADE:SAC salt.
Figure 8:
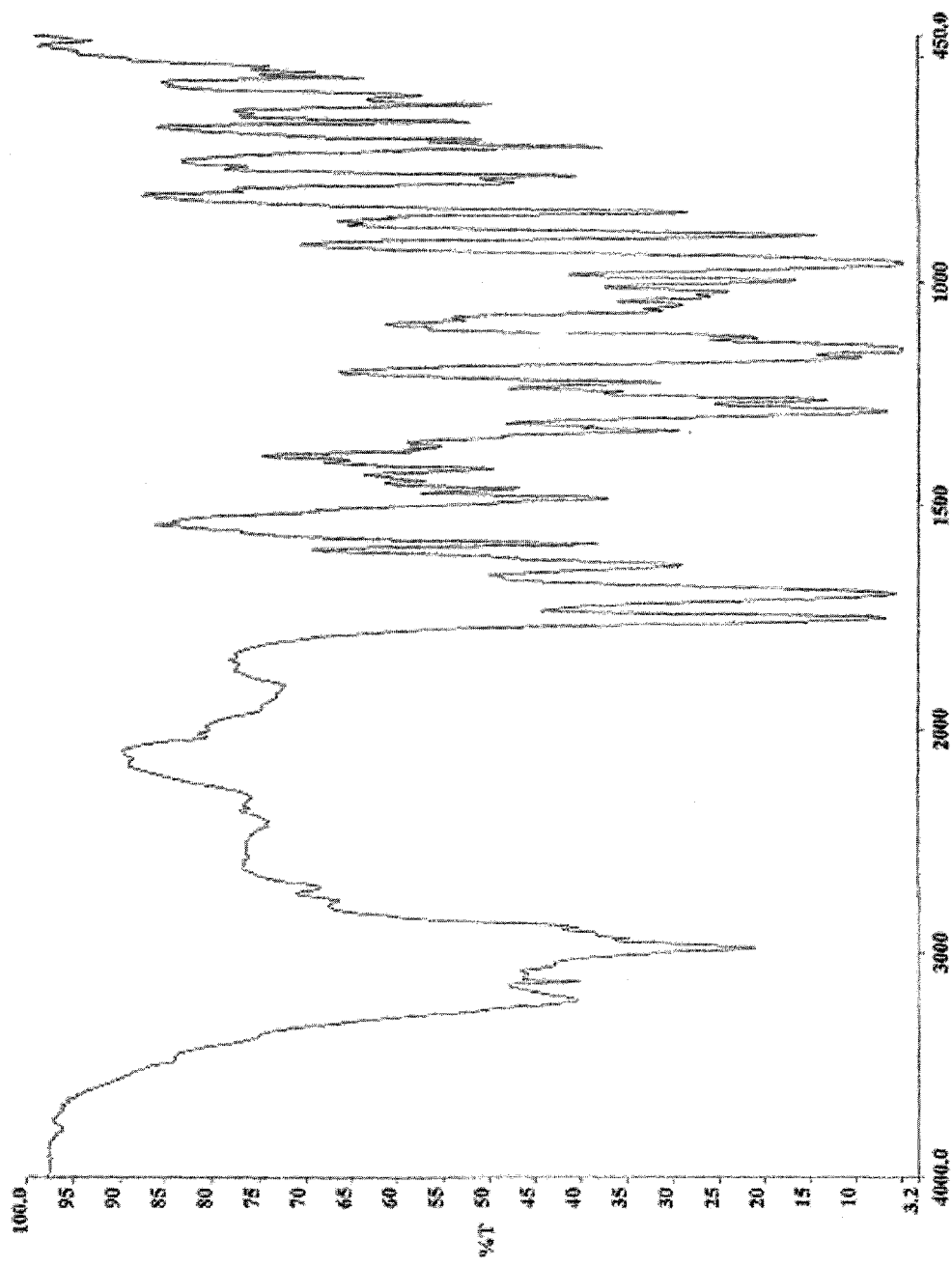
FIG. 8 shows a Fourier transform infrared absorption spectrum of ADE:SAC salt.

Acetone (30 mL) was added to 3.00 g adefovir dipivoxil (0.0060 moles) and 1.11 g saccharin (1.01 equivalents) in a 100 mL round bottom flask at room temperature. Moderate agitation was commenced and the mixture was heated to 40-45° C. A clear solution was achieved after about 15 minutes. Heating was then stopped and the solution was allowed to cool to room temperature. Precipitation of a white solid was observed within 20 minutes. The slurry temperature was adjusted to 30-35° C. and agitation at this temperature was continued 4 hours. The slurry was then allowed to cool to room temperature and was stirred at room temperature for 19 hours. The crystalline solid was collected by suction filtration and dried in vacuo to yield 2.61 g (64%) of ADE:SAC salt. PXRD as shown in FIG. 7. FTIR as shown in FIG. 8.

Example 8

A mixture of 80.00 g adefovir dipivoxil (0.1595 moles) and 29.52 g saccharin (1.01 equivalents) in 550 mL acetone in a 1 L round bottom flask was stirred and heated to 45-50° C. Total dissolution was achieved within 25 minutes. The solution was slowly cooled to 20-25° C. in a controlled manner (over about 4 hours). During the cooling phase precipitation of a white solid was observed. Stirring at room temperature was continued for 16 hours. The slurry was then cooled to 0-5° C. and stirred at that temperature for 5 hours. The salt crystals were collected by suction filtration and dried in vacuo to give 97.88 g (90%) of ADE:SAC salt.

Stability Studies

Whereas the purity of adefovir dipivoxil amorphous decreases by more than 1% after 1 week at 40° C./75% R.H. and 2% after 2 weeks at 40° C./75% R.H., the purity of ADE:NIC cocrystals and ADE:SAC cocrystals remains unchanged after 1 week at 40° C./75% R.H. and suffers only a 0.06% decrease after 4 weeks at 40° C./75% R.H.

While the foregoing provides a detailed description of a preferred embodiment of the invention, it is to be understood that this description is illustrative only of the principles of the invention and not limitative. Furthermore, as many changes can be made to the invention without departing from the scope of the invention, it is intended that all material contained herein be interpreted as illustrative of the invention and not in a limiting sense.

The embodiments of the invention in which an exclusive property or privilege is claimed are as follows:

1. Adefovir dipivoxil and nicotinamide cocrystal.
2. The adefovir dipivoxil and nicotinamide cocrystal of claim 1 having a powder X-ray diffraction ("PXRD") spectrum using Cu—K.alpha radiation expressed in degrees 2 theta showing peaks at 3.6, 7.2, 8.6, 9.1, 10.0, 10.9, 13.7, 15.2, 16.9, 18.2, 20.1, 21.2, 23.7, 24.9, 26.2, 27.7 and 29.3.
3. The adefovir dipivoxil and nicotinamide cocrystal of claim 1 having a PXRD spectrum as shown in FIG. 1.
4. The adefovir dipivoxil and nicotinamide cocrystal of claim 1 having a Fourier Transform Infrared ("FTIR") absorption spectrum (1% KBr) exhibiting peaks expressed in $cm^{-1}$ at about 3421, 3194, 1753, 1647, 1602, 1475, 1400, 1267, 1141 and 962.
5. The adefovir dipivoxil and nicotinamide cocrystal of claim 1 having a FTIR spectrum as shown in FIG. 2.
6. The adefovir dipivoxil and nicotinamide cocrystal of claim 1 having a Differential Scanning calorimetry ("DSC") thermogram having a peak endotherm at a peak onset temperature of about 100° C. and a peak maximum of about 103° C.
7. The adefovir dipivoxil and nicotinamide cocrystal of claim 1 having a DSC thermogram as shown in FIG. 3.
8. A process for preparing a co-crystal of adefovir and nicotinamide cocrystal comprising:
    a) forming a solution of adefovir dipivoxil and nicotinamide in a suitable solvent at an appropriate temperature;
    b) promoting crystal growth;
    c) and collecting the crystals.
9. The process of claim 8, wherein the solvent is selected from the group consisting of $C_3$-$C_{12}$ alkanoic acid esters; $C_3$-$C_7$ alkyl ketones; cyclic and acyclic aliphatic ethers; and $C_1$-$C_8$ alkanols and mixtures thereof.
10. The process of claim 8, wherein the solvent is preferably selected from the group consisting of ethyl acetate, isopropyl acetate, acetone, methyl isobutyl ketone, isopropanol and mixtures thereof.
11. The process of claim 8 wherein the temperature is from about 20° C. to about 70° C.
12. Adefovir dipivoxil and salicylamide cocrystal.
13. The adefovir dipivoxil and salicylamide cocrystal of claim 12 having a PXRD spectrum using Cu—K.alpha radiation expressed in degrees 2 theta showing peaks at 3.3, 6.5, 9.8, 11.9, 12.5, 13.1, 15.0, 15.5, 16.4, 17.7, 21.9, 22.8, 23.6, 24.0, 26.0, 26.8 and 28.3.
14. The adefovir dipivoxil and salicylamide cocrystal of claim 12 having a PXRD spectrum as shown in FIG. 4.
15. The adefovir dipivoxil and salicylamide cocrystal of claim 12 having a FTIR absorption spectrum (1% KBr) exhibiting peaks expressed in $cm^{-1}$ at about 3411, 3162, 2987, 1755, 1677, 1603, 1415, 1271, 1154 and 972.
16. The adefovir dipivoxil and salicylamide cocrystal of claim 12 having a FTIR spectrum as shown in FIG. 5.
17. The adefovir dipivoxil and salicylamide cocrystal of claim 12 having a DSC thermogram having a peak endotherm at a peak onset temperature of about 108° C. and a peak maximum of about 109° C.
18. The adefovir dipivoxil and salicylamide cocrystal of claim 12 having a DSC thermogram as shown in FIG. 6.
19. A process for preparing a co-crystal of adefovir and salicylamide comprising:
    a) forming a solution of adefovir dipivoxil and salicylamide in a suitable solvent at an appropriate temperature;
    b) promoting crystal growth;
    c) and collecting the crystals.
20. The process of claim 19, wherein the solvent is selected from the group consisting of $C_3$-$C_{12}$ alkanoic acid esters; $C_3$-$C_7$ alkyl ketones; cyclic and acyclic aliphatic ethers; and mixtures thereof.
21. The process of claim 19, wherein the solvent is preferably selected from the group consisting of ethyl acetate, acetone, methyl tert-butyl ether and mixtures thereof.
22. The process of claim 19, wherein the temperature is from about 20° C. to about 65° C.

* * * * *